(12) United States Patent
Beaven

(10) Patent No.: US 11,759,101 B2
(45) Date of Patent: *Sep. 19, 2023

(54) RETRACTOR FOR VAGINAL REPAIR

(71) Applicant: Modern Surgical Solutions LLC, Covington, KY (US)

(72) Inventor: Richard B. Beaven, Covington, KY (US)

(73) Assignee: Modern Surgical Solutions LLC, Covington, KY (US)

(*) Notice: Subject to any disclaimer, the term of this patent is extended or adjusted under 35 U.S.C. 154(b) by 288 days.

This patent is subject to a terminal disclaimer.

(21) Appl. No.: 17/306,268

(22) Filed: May 3, 2021

(65) Prior Publication Data
US 2021/0267449 A1    Sep. 2, 2021

Related U.S. Application Data

(63) Continuation-in-part of application No. 16/354,597, filed on Mar. 15, 2019, now Pat. No. 11,026,671.

(51) Int. Cl.
*A61B 1/303* (2006.01)
*A61B 1/32* (2006.01)
*A61B 17/42* (2006.01)
*A61B 17/02* (2006.01)

(52) U.S. Cl.
CPC ............... *A61B 1/32* (2013.01); *A61B 1/303* (2013.01); *A61B 17/42* (2013.01); *A61B 2017/0212* (2013.01)

(58) Field of Classification Search
CPC .... A61B 2017/0237; A61B 2017/3429; A61B 2017/0212; A61B 2017/0225; A61B 17/3431; A61B 17/3429; A61B 17/02-0206; A61B 17/218; A61B 1/303; A61B 1/32

See application file for complete search history.

(56) References Cited

U.S. PATENT DOCUMENTS

| | | | | |
|---|---|---|---|---|
| 40,949 | A * | 12/1863 | Scattergood | A61F 6/08 128/834 |
| 2,536,145 | A * | 1/1951 | Tapke | A61B 90/00 606/205 |
| 2,664,082 | A * | 12/1953 | Heuboski | A61F 6/08 128/837 |

(Continued)

*Primary Examiner* — Eduardo C Robert
*Assistant Examiner* — Michelle C Eckman
(74) *Attorney, Agent, or Firm* — Ronald J. Richter; Nesbitt IP LLC

(57) ABSTRACT

A self-expanding retractor is described for placement within the vaginal canal of a post-partum female to aid in performing a vaginal repair. The retractor provides improved exposure and enhanced visualization of an episiotomy or vaginal laceration repair site. The retractor is typically in the form of a foldable, trapezoidal frame defining a central aperture, and includes anterior stability posts at its corners and a panel spanning the central aperture. The panel is typically in the form of a surgical gauze pad for absorbing blood and fluids entering the surgical field. The retractor can be folded by a user for placement within the vaginal canal and then released, which allows it to expand to hold back swollen tissues from obstructing the repair site. The retractor is typically lightweight and compact and is configured to minimize slippage during use.

18 Claims, 7 Drawing Sheets

(56) References Cited

U.S. PATENT DOCUMENTS

| | | | | |
|---|---|---|---|---|
| 3,129,706 | A * | 4/1964 | Reynolds, Jr. | A61B 17/0293 600/233 |
| 5,334,217 | A * | 8/1994 | Das | A61B 17/0057 606/151 |
| 5,562,690 | A * | 10/1996 | Green | A61B 17/11 606/154 |
| 6,216,698 | B1 * | 4/2001 | Regula | A61F 6/08 128/830 |
| 11,026,671 | B2 * | 6/2021 | Beaven | A61B 17/42 |
| 2006/0004261 | A1 * | 1/2006 | Douglas | A61B 1/32 600/210 |
| 2009/0326331 | A1 * | 12/2009 | Rosen | A61B 1/32 600/224 |
| 2013/0018229 | A1 * | 1/2013 | Jaworek | A61B 17/0218 600/206 |
| 2013/0190558 | A1 * | 7/2013 | Alexander | A61B 1/32 600/37 |
| 2014/0200409 | A1 * | 7/2014 | Green | A61B 17/0293 600/208 |
| 2014/0276900 | A1 * | 9/2014 | Cote | A61F 9/007 606/107 |
| 2015/0351736 | A1 * | 12/2015 | Bhattacharjee | A61B 17/0231 600/209 |
| 2016/0051244 | A1 * | 2/2016 | Akura | A61B 17/0206 600/236 |

\* cited by examiner

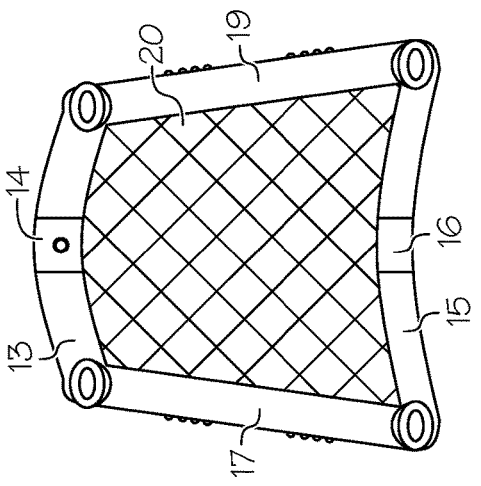
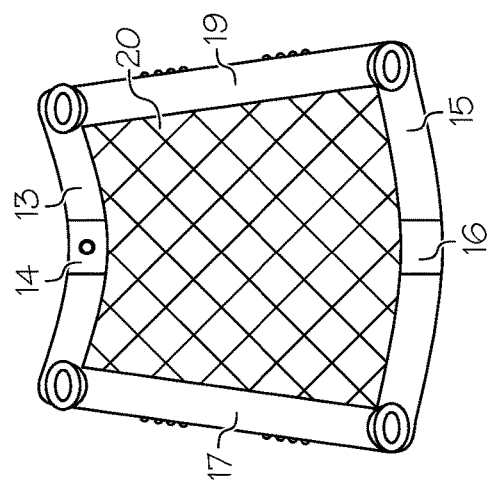
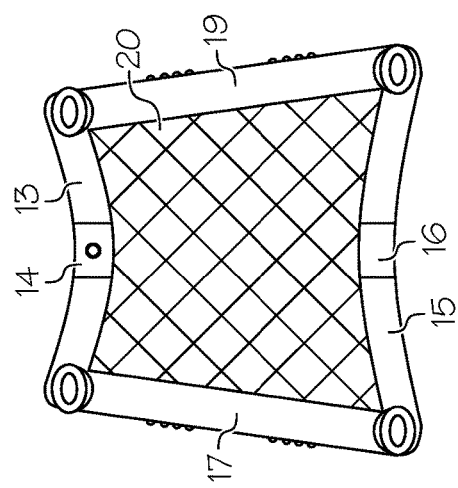
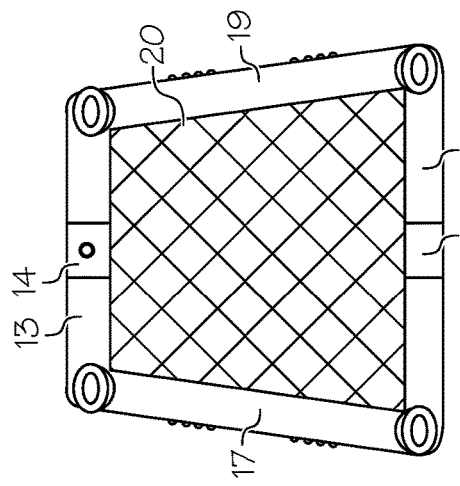
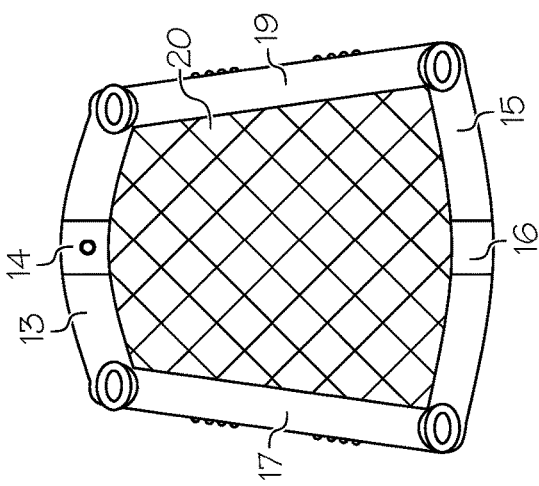

RETRACTOR FOR VAGINAL REPAIR

CROSS-REFERENCE TO RELATED APPLICATION

The present application claims the benefit of U.S. application Ser. No. 16/354,597 filed Mar. 15, 2019, the disclosure of which is hereby incorporated by reference in its entirety.

FIELD OF THE INVENTION

The present invention relates generally to obstetric surgical instruments, and more particularly to a retractor which provides improved exposure for working about the perineum and vaginal walls of a post-partum patient.

BACKGROUND OF THE INVENTION

Lacerations of the vaginal walls and the perineum commonly occur during vaginal delivery. In addition, sometimes an episiotomy, i.e. a surgical cut made at the vaginal opening, is made by a health care professional such as an obstetric surgeon or midwife to enlarge the vaginal opening during childbirth. Typically an episiotomy is made through the posterior vaginal wall and the perineum, i.e. between the vaginal opening and the anus. Although an episiotomy was once common practice, due to the increased risk of infection and other complications the current recommendations are to perform such an incision only when necessary. Therefore, an episiotomy will typically only be performed to aid a difficult delivery or to prevent rupture of tissues. Nevertheless, even when an episiotomy is not performed, vaginal delivery may still cause stretching, tearing and lacerations of the vaginal walls and perineum, which will need to be repaired.

An episiotomy incision or vaginal laceration should be repaired promptly following childbirth to reduce blood loss and prevent infection. The health care professional will initially examine the tissues to determine the extent of repair needed, and repair of the incised or lacerated tissues is then typically performed by placement of sutures, which absorb over time. Adequate pain relief should be provided before suturing, and this is typically done via injection of a local anesthetic into the skin and muscle in and around the surgical area to numb the tissues.

Typical prior art vaginal retractors are speculum-type retractors, in which a pair of metal blades are connected to a body with handles for opening and closing the blades. The blades are typically smooth and thin metal plates with dull edges that are inserted into the vaginal canal and then opened to pull back the tissue. In use, the blades are first placed into a closed position in which they are in close proximity to one another for insertion into the vaginal canal, and the blades are then displaced by the handles to assume an open position which spreads apart the tissues. Such retractors are typically useful for performing pelvic examinations on non-laboring females, but they can also be used to create a surgical workspace for post-partum laceration repair.

While useful, prior art bladed or speculum-type vaginal retractors have not proven to be entirely satisfactory for post-partum laceration repair. For example, the delivering mother's labia typically are engorged and swollen as compared to a non-parturient female, and standard bladed retractors are generally not satisfactory because the swollen labia can expand around the blades and impinge on the field of vision, making the repair more difficult. In addition, the metal blades and their handles can be cold and heavy, and, since the handles typically suspend externally from the vagina during the repair, their weight can cause the retractor to slip or displace. In addition, the externally suspended handles often obstruct the range of movement of the surgeon, causing the sutures to become entangled about the handles. Bladed retractors are also difficult to use if there is a laceration of the vaginal side wall or sulcus, since in practice the blades are typically inserted against the side walls of the vagina prior to opening the blades. As a result the blades must be manipulated or even removed in order to gain access to the laceration and finish the repair. Such limitations of an already difficult and bloody work area generally makes repair more difficult and time-consuming, leading to increased blood loss, incomplete repair, and infection.

In addition to the physical limitations noted above when using speculum-type retractors for post-partum laceration repair, the limited exposure they do provide is often distorted or clouded by inflowing blood and other fluids entering the surgical field from the cervix and uterus, which is common following vaginal delivery. As a result, the surgeon will often place a gauze pad or a surgical sponge into the vagina during the repair procedure in order to absorb these fluids and improve visualization. However, secondary sponge placement can also lead to complications, such as entanglement of the sponge with the retractor or the sutures. In addition, there is the potential that the sponge, which is not attached to the retractor, can be inadvertently left inside the vagina after the repair, creating a nidus for infection.

In view of the above discussion, it is apparent that there is a need in the obstetric surgical arts to provide an improved apparatus and method for performing a post-partum vaginal laceration or episiotomy repair. It would therefore be advantageous to provide a vaginal retractor which improves access and visualization of the repair site, is configured to minimize slippage during use, and which is lightweight and minimizes discomfort to the patient. It would also be advantageous to provide a vaginal retractor with a means to absorb or prevent blood and other fluids entering the surgical field. It would also be beneficial to provide a vaginal retractor which can be utilized by health care professionals having various skill levels.

SUMMARY OF THE INVENTION

Briefly stated, a retractor for vaginal repairs according to the different embodiments of this invention can provide sufficient visualization of lacerated tissues of the post-partum perineum and vaginal walls.

One aspect of the invention provides a retractor for use in performing a repair of a vaginal laceration, the retractor comprising: (a) a foldable frame defining a central aperture and including an upper support, a lower support, a right lateral support, a left lateral support, a right upper anterior stability post, a left upper anterior stability post, a right lower anterior stability post, and a left lower anterior stability post; and (b) a compliant panel spanning the central aperture, wherein the frame is biased to assume an open position, can be folded by a user into a closed position for insertion into the vaginal canal, and can then return to the open position after release by the user.

Another aspect of the invention provides a retractor for performing a repair of a vaginal laceration, the retractor comprising: (a) a foldable frame defining a central aperture, the frame including: (i) an upper support including a central upper crimp; (ii) a lower support including a central lower crimp, wherein the central upper crimp and the central lower crimp are biased to bend when a force is applied by a user and to straighten when the force is released; (iii) a right lateral support; (iv) a left lateral support, wherein the upper support, the lower support, the right lateral support, and the left lateral support are connected to form the frame defining the central aperture; (v) a right upper anterior stability post; (vi) a left upper anterior stability post; (vii) a right lower anterior stability post; and (viii) a left lower anterior stability post; and (b) a compliant panel spanning the central aperture, wherein the frame is biased to assume an open position, can be folded by a user into a closed position for insertion into the vaginal canal, and can then return to the open position after release by the user.

Another aspect of the invention provides a method of performing a repair of a vaginal laceration, the method comprising the steps of: (a) providing a vaginal retractor, the retractor comprising: (i) a foldable frame defining a central aperture and including an upper support, a lower support, a right lateral support, a left lateral support, a right upper anterior stability post, a left upper anterior stability post, a right lower anterior stability post, and a left lower anterior stability post, wherein the frame is biased to assume an open position; and (ii) a compliant panel spanning the central aperture; (b) folding the frame into a closed position; (c) inserting the frame into the vaginal canal; (d) releasing the frame to expand to the open position within the vaginal canal; and (e) repairing the vaginal laceration by suturing the lacerated tissue layers.

Another aspect of the invention provides a retractor for gynecological procedures involving the lower internal genital organs, the retractor comprising: (a) a frame defining a central aperture, the frame including an upper support, a lower support, a right lateral support, a left lateral support, a right upper anterior stability post, a left upper anterior stability post, a right lower anterior stability post, and a left lower anterior stability post, wherein the frame is biased to assume an open position in which the supports are oriented substantially in a single plane, and wherein each of the anterior stability posts extend substantially perpendicularly from the plane of the open frame; and (b) a plurality of walls for restraining vaginal tissues from obstructing the central aperture, wherein each of the plurality of walls is connected to the frame and extends substantially perpendicularly from the plane of the open frame, and wherein the frame can be folded into a closed position for insertion into the vaginal canal.

Another aspect of the invention provides a retractor for gynecological procedures involving the lower internal genital organs, the retractor comprising: (a) a frame defining a central aperture, the frame including: (i) an upper support including a central upper crimp; (ii) a lower support including a central lower crimp, wherein the central upper crimp and the central lower crimp are biased to bend when a force is applied by a user and to straighten when the force is released; (iii) a right lateral support; (iv) a left lateral support, wherein the upper support, the lower support, the right lateral support, and the left lateral support are connected to form the frame defining the central aperture; (v) a right upper anterior stability post; (vi) a left upper anterior stability post; (vii) a right lower anterior stability post; and (viii) a left lower anterior stability post; wherein the frame is biased to assume an open position in which the supports are oriented substantially in a single plane, and wherein each of the anterior stability posts extend substantially perpendicularly from the plane of the open frame; and (b) a plurality of walls for restraining vaginal tissues from obstructing the central aperture, wherein each of the plurality of walls is connected to and extends substantially perpendicularly from the plane of the open frame, the plurality of walls comprising: (i) a right side wall located between the right upper anterior stability post and the right lower anterior stability post; (ii) a left side wall located between the left upper anterior stability post and the left lower anterior stability post; and (iii) an upper wall located between the right upper anterior stability post and the left upper anterior stability post, wherein the frame can be folded into a closed position for insertion into the vaginal canal.

The nature and advantages of the present invention will be more fully appreciated after reviewing the accompanying drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

FIGS. 6A-6E illustrate various curvature orientations of the upper and lower supports of the inventive retractor;

DETAILED DESCRIPTION OF THE INVENTION

As used herein, terms such as laceration, tear, cut, incision, "lacerated tissues", "vaginal laceration" or "episiotomy incision", although technically different in nature and created in different ways, are understood to be interchangeable.

As used herein, terms such as fold, foldable, folded, collapse, collapsible and collapsed are understood to be interchangeable when referring to either the upper and lower supports or the frame being in, or assuming, a "closed" position.

Figure 1:
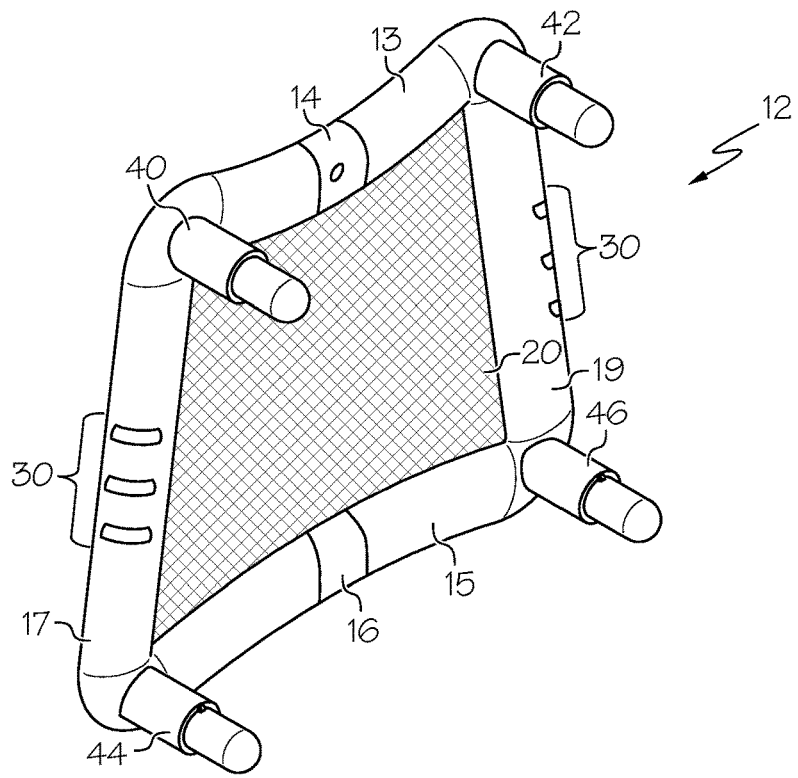
FIG. 1 is a frontal view of one embodiment of the inventive retractor.
Figure 2:
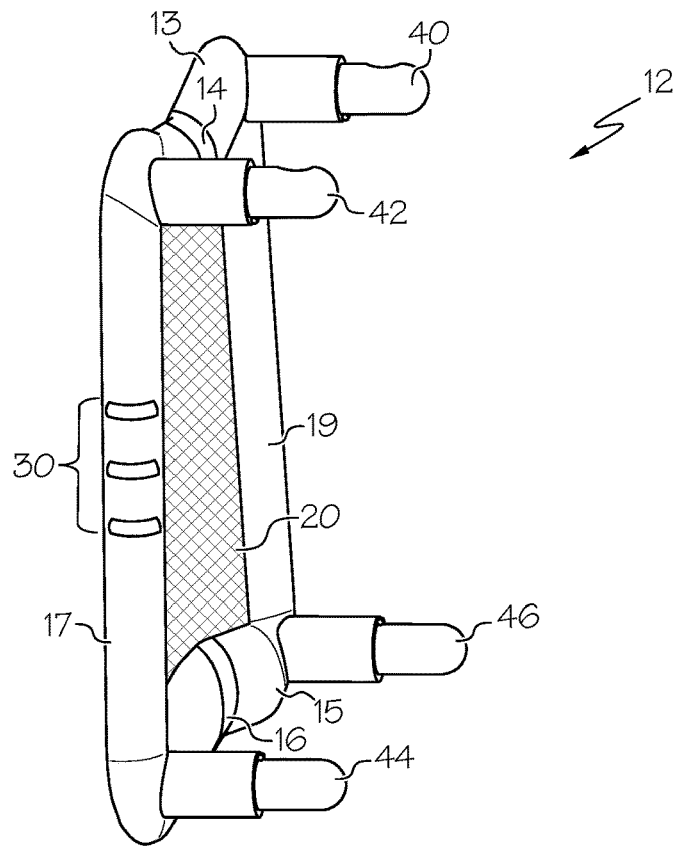
FIG. 2 is a right lateral view of the retractor of FIG. 1.
Figure 3A:
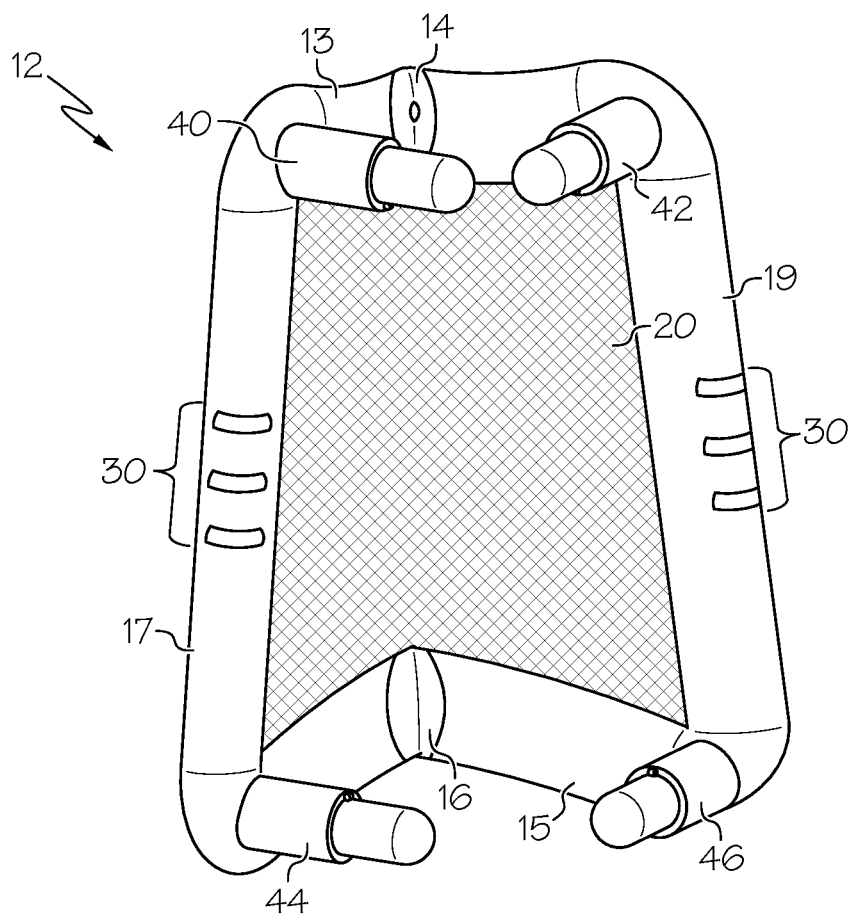
FIG. 3A is a frontal view showing the retractor of FIG. 1 when in the collapsed position.
Figure 3B:
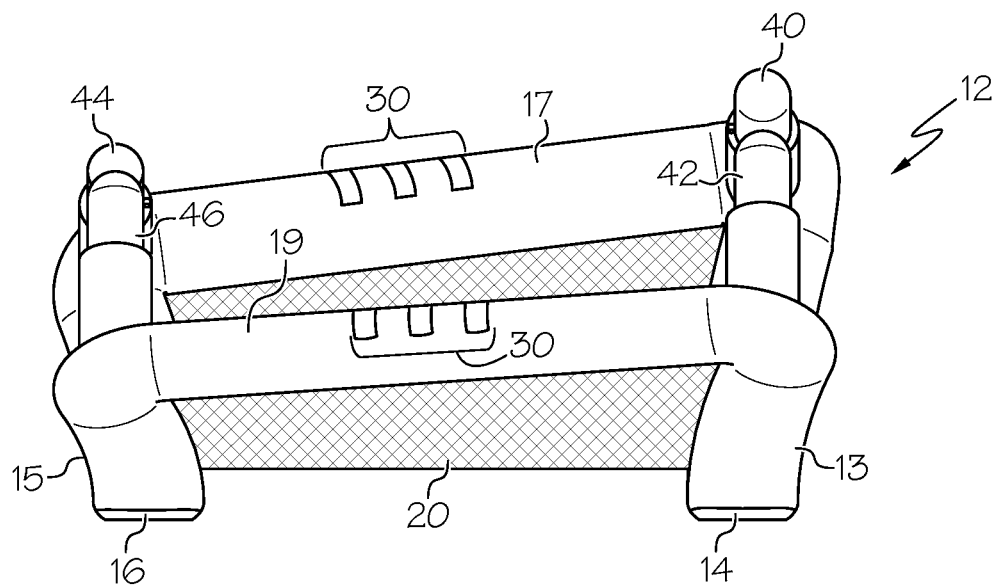
FIG. 3B is a side view of the collapsed retractor of FIG. 3A laying on its back.

A preferred embodiment of the inventive retractor is illustrated in FIGS. 1, 2, 3A and 3B, which show a foldable frame 12. The frame 12 is biased or predisposed to take an expanded or "open" position as shown in FIGS. 1 and 2, but can be folded or otherwise manually compressed or collapsed by a user into a "closed" position as shown in FIGS. 3A and 3B. Looking at FIGS. 1 and 2, both the upper support 13 and the lower support 15 include a bendable central crimp, 14 and 16, respectively. More specifically, the central upper crimp 14 and the central lower crimp 16 bend when a force is applied by a user, and they straighten when the force is released. The central upper crimp 14 and the central lower crimp 16 are preferably made of a semi-rigid but flexible plastic material, so while biased to assume a substantially straight or unfolded orientation, they can be caused to bend when a manual force is applied by a user. Such an applied force can bend the crimps 14, 16 so that their corresponding upper and lower supports 13, 15 fold in upon themselves, causing the frame 12 to fold as well, assuming the closed position as illustrated in FIGS. 3A and 3B. When the force is removed, i.e. by releasing the frame, the crimps 14, 16 will then straighten out and the retractor re-expands to the "open" position.

The frame 12 is preferably intended to be positioned within the introitus, or entrance, of the vaginal canal, or slightly deeper into the vaginal canal if needed, to provide improved exposure and access to the surgical field, and is typically folded into the closed position prior to and during insertion into the vaginal entrance. Once inserted and released, the frame 12 will expand on its own assume the open position. The frame 12 is defined by an upper support 13, a lower support 15, a right lateral support 17, and a left lateral support 19. The supports 13, 15, 17 and 19 are preferably connected at their ends to form a trapezoidal-shaped frame 12 defining a central aperture 20 within its inner perimeter.

As best seen in FIG. 1, when the frame 12 is in its biased "open" position, the supports 13, 15, 17, 19 are oriented substantially in a single plane and the central aperture 20 is substantially filled by a panel 20. The panel 20 is typically attached to or otherwise secured to the frame, substantially spanning the central aperture, and is preferably compliant with the frame, i.e. it is generally thin and flexible and acquiesces or yields to the opening and closing movements of the frame. The panel 20 aids the user in visualization of the surgical field, i.e. the lacerated vaginal and perineal tissues of the post-partum mother (see FIG. 4), by absorbing or otherwise averting fluids from entering. In a preferred embodiment the panel 20 is an absorbent pad made of cotton, surgical gauze, a surgical sponge or other similar compliant and semi-permeable material useful for substantially absorbing blood and other fluids passing through the central aperture. In another embodiment (not shown) the panel can be made of a plastic membrane, net or other similar substantially non-permeable material useful for preventing entrance/passage of blood and other fluids through the central aperture.

In a preferred embodiment the retractor frame 12 and the panel 20 are manufactured together, such that the panel comes pre-installed and spans the central aperture of the frame. In this manner, the retractor is ready to use without additional steps needed to load the panel into the retractor frame prior to use. The panel can also be manufactured to envelope the frame or be stretched around the supports 13, 15, 17 and 19. In one embodiment a second panel (not shown), in the form of either a semi-permeable material such as an absorbent pad or a non-permeable material such as a plastic membrane, can be secured to the frame along with the initial panel. Inclusion of a second panel may be useful for improved visibility, should the user anticipate oversaturation of the surgical field with blood or fluids from the vaginal canal during the repair procedure.

The frame supports 13, 15, 17 and 19 are typically rigid plastic structures and are preferably connected at their corners to form a unitary, trapezoidal-shaped frame 12. Each of the four corners of the frame 12 have projections, specifically, a right upper anterior stability post 40, a left upper anterior stability post 42, a right lower anterior stability post 44, and a left lower anterior stability post 46. The anterior stability posts 40, 42, 44, 46 are preferably made of a rigid plastic like the frame supports, and extend substantially perpendicularly from the plane of the open frame 12. In contrast, the bendable central crimps 14 and 16 are necessarily less rigid in nature than the frame supports and the anterior stability posts, and are typically made of a soft plastic or elastomer which bends to allow their respective supports 13, 15 to be folded when a manual force is applied by the user.

The frame supports 13, 15, 17, 19 and the anterior stability posts 40, 42, 44, 46 function to support and retract the swollen tissues during use, so that the laceration 50 (see FIG. 4) can be visualized, accessed, and repaired. As seen in FIG. 2, the right and left upper stability posts 40, 42 can include a divot along their length to receive and support the pubic bone. The anterior stability posts 40, 42, 44, 46 in the embodiment shown in FIGS. 1, 2, 3A and 3B are telescopic in nature, and function to retract and hold back the swollen labia and/or other vaginal tissues from interfering with visualization of the surgical field. In use, the telescopic posts can be manually shortened prior to folding the frame into the closed position, and then extended out by the user after the frame re-opens. The anterior stability posts' ability to extend out is useful for providing labial retraction; nevertheless, in situations in which the laceration 50 requires the retractor to be placed deeper than normal within the vaginal canal, the anterior stability posts may not be able to fully retract the labia, but they can still support the labia to some degree as well as hold back the swollen tissues within the vaginal canal to provide adequate visualization of the surgical field.

As can be seen in FIGS. 1, 2, 3A and 3B, each of the lateral supports 17, 19 can include a set of stability ridges 30, typically in the form of a series of raised semi-circular edges protruding between about 1 mm (millimeters) to about 3 mm from the outer perimeter of the lateral supports. The stability ridges 30 serve to hold the retractor in place, i.e. in its position within the vaginal canal, by virtue of the rough surfaces created by the raised edges. They are included to counteract slippage of the frame during use by increasing the amount of friction between the vaginal tissue and the retractor.

As illustrated in FIGS. 3A and 3B, bending of the flexible crimps 14, 16 can cause the frame 12 to assume the closed position. Specifically, when a manual force is applied by the user to bend the crimps 14, 16, the corresponding upper and lower supports 13, 15 fold in upon themselves. When the force is removed, i.e. by releasing the frame, the retractor re-expands to the "open" position illustrated in FIGS. 1, 2 and 4. The compliant panel 20, being made of a generally thin and flexible material, folds along with the frame 12. As shown in FIGS. 3A and 3B, in this closed position the right lateral 17 and the left lateral 19 supports come into close proximity with each other, as do the upper 40, 42 and lower 44, 46 anterior stability posts (which can be shortened, if telescopic). This closed position easily allows for placement and positioning of the collapsed retractor into the vaginal canal by the user. Once the retractor is properly positioned, the user can release the retractor, allowing the crimps 14, 16 to straighten and return the frame to the "open" position (see FIGS. 1, 2 and 4).

While the crimps 14, 16 provide the frame 12 with the ability to be folded or collapsed into the closed position, it should be noted that the foldable retractor described herein is not limited to this means of folding. For example, rather than employing crimps, each of the corners of the frame can be made of a semi-rigid but flexible plastic material which allows the frame to be contorted or otherwise twisted at the corners, causing the frame to collapse and/or fold into the closed position. Alternatively, the corners may be constructed to be "hinged" in such a way that the frame collapses or folds into the closed position.

Figure 4:
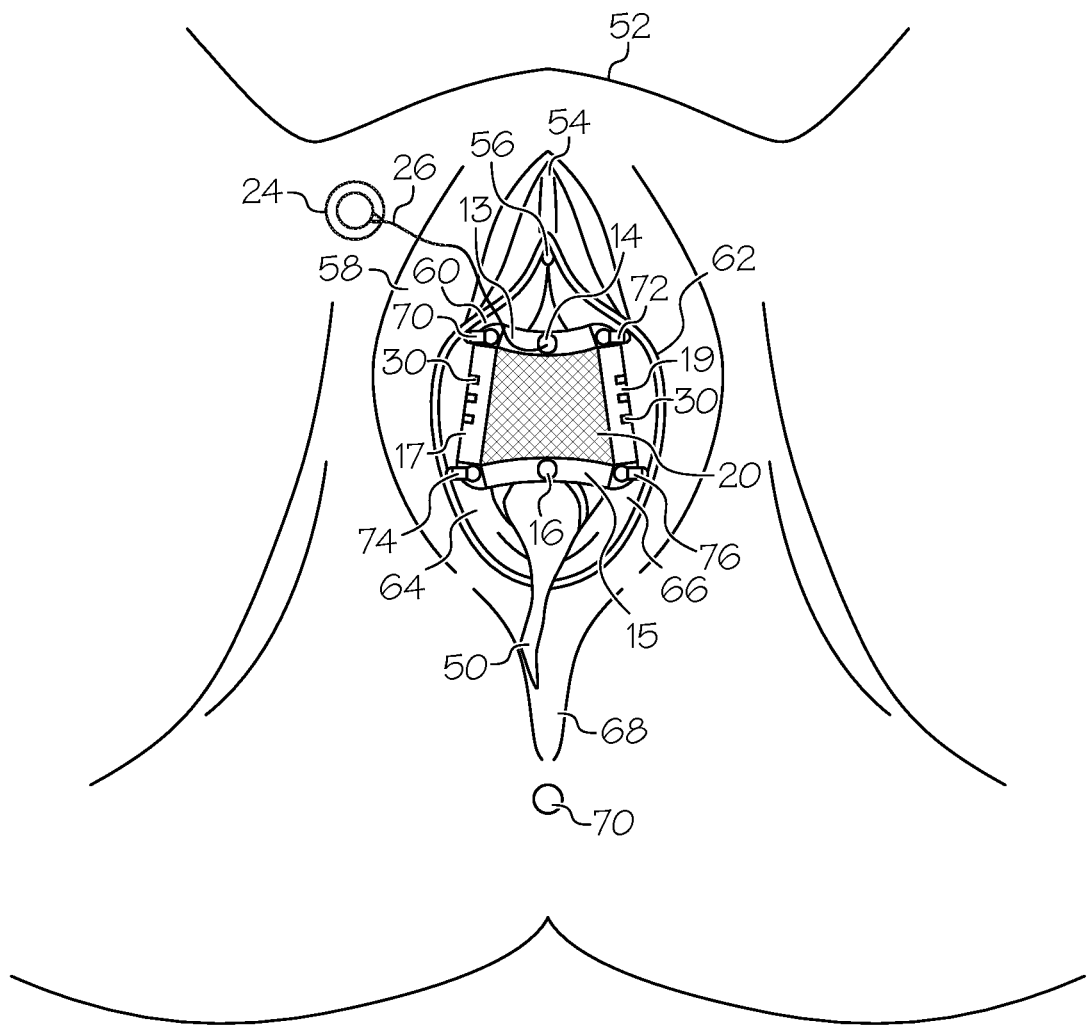
FIG. 4 is a perspective view of the inventive retractor of FIG. 1 positioned within the vagina of a patient with a vaginal laceration.
Figure 5:
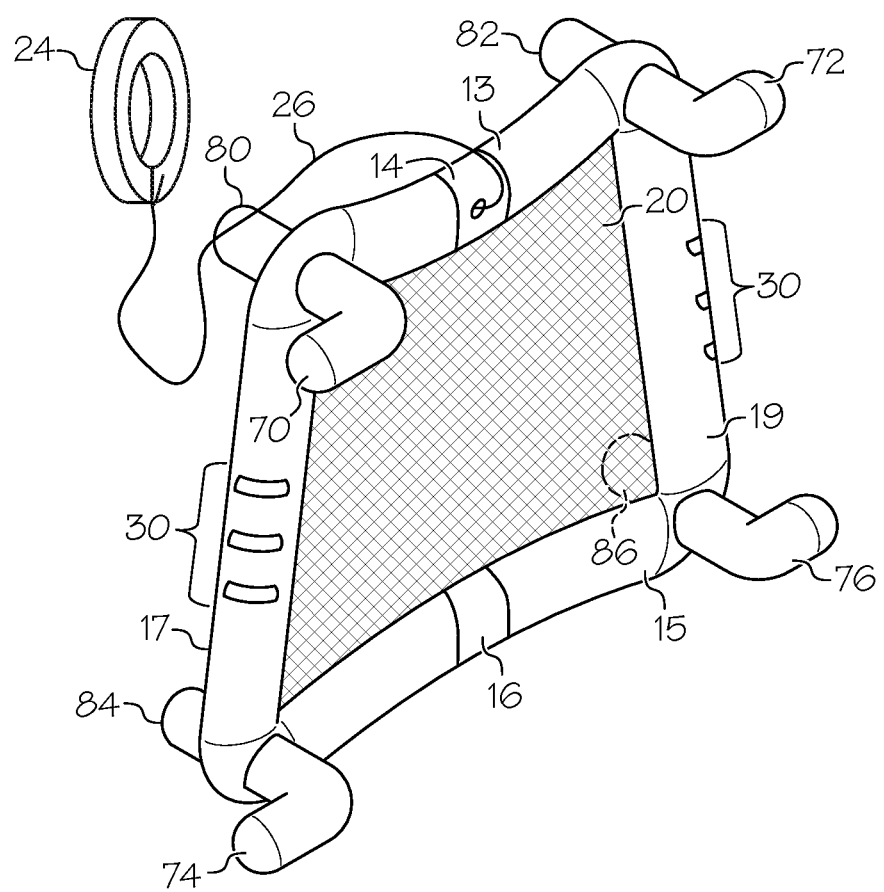
FIG. 5 is a frontal view of a further embodiment of the inventive retractor.

FIGS. 4 and 5 illustrate an embodiment of the retractor frame having anterior stability posts 70, 72, 74, 76 which are outwardly curved or otherwise biased in an outward direction. This curved design provides an additional means to hold back swollen vaginal or labial tissues which may be entering the surgical field. Further, both FIG. 4 and FIG. 5 illustrate an optional ring 24 attached to the frame by a string 26. The ring can aid in the retrieval of a lost or retained retractor, should it somehow become dislodged and lost within the vaginal canal. The frame supports 13, 15, 17, 19 and/or the ring 24 can contain RFID scanning technology as is known in the art, which can be used to identify a retained product and aid in retrieval.

During use, and after being folded into the closed position and inserted at the entrance of the vaginal canal and behind the laceration site 50, the folded retractor frame is released by the user. The crimps 14, 16 assume their original straight shape per their bias, and the frame supports 13, 15 expand, so that the retractor assumes the open position. Looking at FIG. 4, a typical surgical field amenable for using the inventive retractor includes an episiotomy incision/vaginal laceration 50 located in the area including the posterior vaginal wall 64 and the perineum 68, i.e. the area of skin and muscular tissue between the posterior vaginal wall 64 and the anus 70. The frame 12 is placed by the surgeon into the vaginal introitus, located beneath the pubic bone 52, the clitoris 54 and the urethral opening 56. The right and left upper anterior stability posts 70, 72 secure the frame between the right and left anterior sulci 60, 62 of the anterior vaginal wall above, while the right and left lower anterior stability posts 74, 76 secure the frame between the right and left posterior sulci 64, 66 of the posterior vaginal wall below. This positioning serves to prevent slippage of the retractor frame within the vaginal canal during the repair procedure. After expansion, the retractor frame 12 is completely out of the way of the surgeon and provides the exposure needed for visualization of the laceration and suture placement. In addition, the retractor's panel 20 provides a barrier to blood and fluids flowing into the surgical field.

As seen in the embodiment illustrated in FIG. 5, the retractor can also include posterior stability posts 80, 82, 84, 86, which extend from the frame 12 in substantially the opposite direction as the anterior stability posts 70, 72, 74, 76. Specifically, as shown in FIG. 5, the retractor frame can include a right upper posterior stability post 80, a left upper posterior stability post 82, a right lower posterior stability post 84, and a left lower posterior stability post 86 respectively corresponding to the right upper anterior stability post 70, the left upper anterior stability post 72, the right lower anterior stability post 74, and the left lower anterior stability post 76. The posterior stability posts are typically shorter than the anterior posts, but nevertheless can assist in retraction as well as prevent slippage or backward movement of the frame within the vaginal canal.

The inventive retractor is intended to be of appropriate size and shape to be placed within the vaginal introitus of a human or mammalian female, with the specific size needed being determined by the particular subject. For example, in the open position the frame 12 may establish a perimeter of about 5 cm to about 40 cm, inclusive of all dimensions within this range. In a preferred embodiment, the lower support 15 and the right and left lateral supports 17, 19 are substantially the same length (e.g. 3-10 cm long), while the upper support 13 is shorter (e.g. 1-7 cm long), so that the overall shape of the frame is trapezoidal when in the open position. In the inventor's experience, this trapezoidal shape best fits the anatomy and natural contours created by the various support ligaments, muscles, soft tissues and membranes forming the vaginal canal.

FIGS. 6A-6E illustrate various different configurations of a trapezoid-shaped retractor in the open position in which there are differing orientations of the curve of the top and bottom supports 13, 15. FIG. 6A shows the preferred embodiment shown in FIGS. 1 and 2 with the upper support 13 having its central portion curved downward and the lower support 15 curved upward, while FIG. 6B shows both supports 13, 15 having their central portion curved downward, FIG. 6C shows both supports 13, 15 having their central portion curved upward, FIG. 6D shows the upper support 13 having its central portion curved upward and the lower support 15 curved downward, and FIG. 6E shows both supports 13, 15 having a straight orientation. Depending on the specific anatomy of the subject, these specific support curvatures can be used while still maintaining the general trapezoidal shape of the retractor to provide an optimal fit within the vaginal canal.

The frame supports 13, 15, 17, 19 can be made of a hard rubber, semi-rigid plastic or hard plastic, while the crimps 14, 16 can be made of a more flexible, elastic material such as silicone rubber, semi-rigid plastic or other elastomer. The "Shore A" or durometer hardness value of the supports 13, 15, 17, 19 is typically higher (i.e. harder) than the crimps 14, 16, which are more elastic. As a non-limiting example, the crimps can be of soft to medium hardness (e.g. 35-60 Shore A) so that they can be bendable but, as noted above, biased to returned to a substantially straight configuration, while the supports are more rigid and can measure on the high end of the hardness scale (e.g. 75-100 Shore A).

The stability posts 40, 42, 44, 46 are also rigid plastic structures on the high end of the hardness scale (e.g. 75-100 Shore A), and they can be attached to the frame by various means as is known in the art. For example, the stability posts can be manufactured along with the frame supports as a unitary frame structure, extending substantially perpendicularly from the frame at each of the corners. In other embodiments, the stability posts can be screwed on, snapped on, or otherwise attached after being separately manufactured apart from the frame structure.

The panel 20, when in its preferred form of an absorbent pad, is preferably made of surgical gauze. Surgical gauze is typically made from fibers of cotton, rayon, polyester, or a combination of these fibers. In the U.S., surgical gauze must meet standards of purity, thread count, construction, and sterility. The particular type of gauze can be woven or nonwoven, sterile or non-sterile, plain or impregnated with pharmaceutical materials, and can be available in various thicknesses. Woven gauze has a loose, open weave, which allows fluids to be absorbed into the fibers. Most woven products are a fine or coarse cotton mesh. Nonwoven gauze consists of fibers pressed together, which provides improved wicking and greater absorbent capacity. Compared to woven gauze, this type of gauze produces less lint and has the benefit of leaving fewer fibers behind in a wound when removed. Most nonwoven gauze is made of polyester, rayon, or blends of these fibers and is stronger, bulkier, and softer than woven pads. Both woven and nonwoven gauze pads are useful for blood absorbency.

Figure 7:
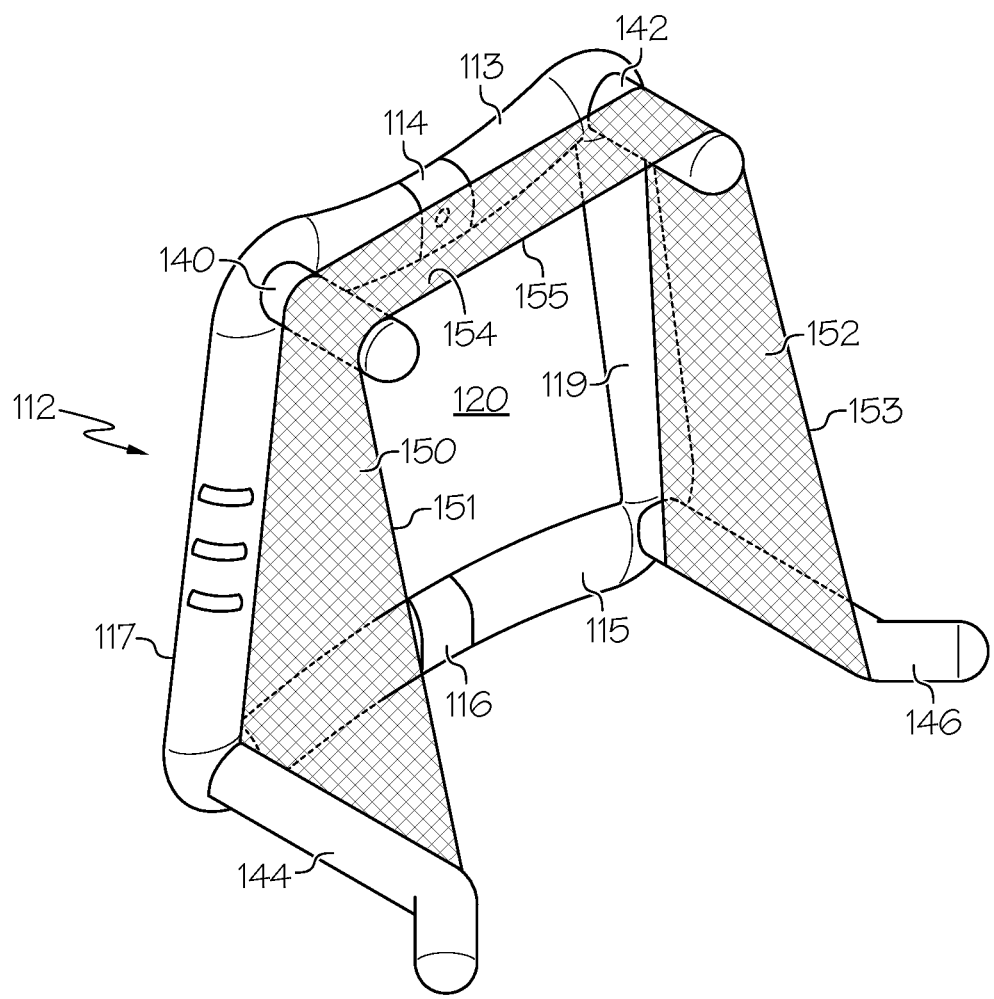
FIG. 7 is a frontal perspective view of an alternative embodiment of the inventive retractor having 3 side walls.
Figure 8:
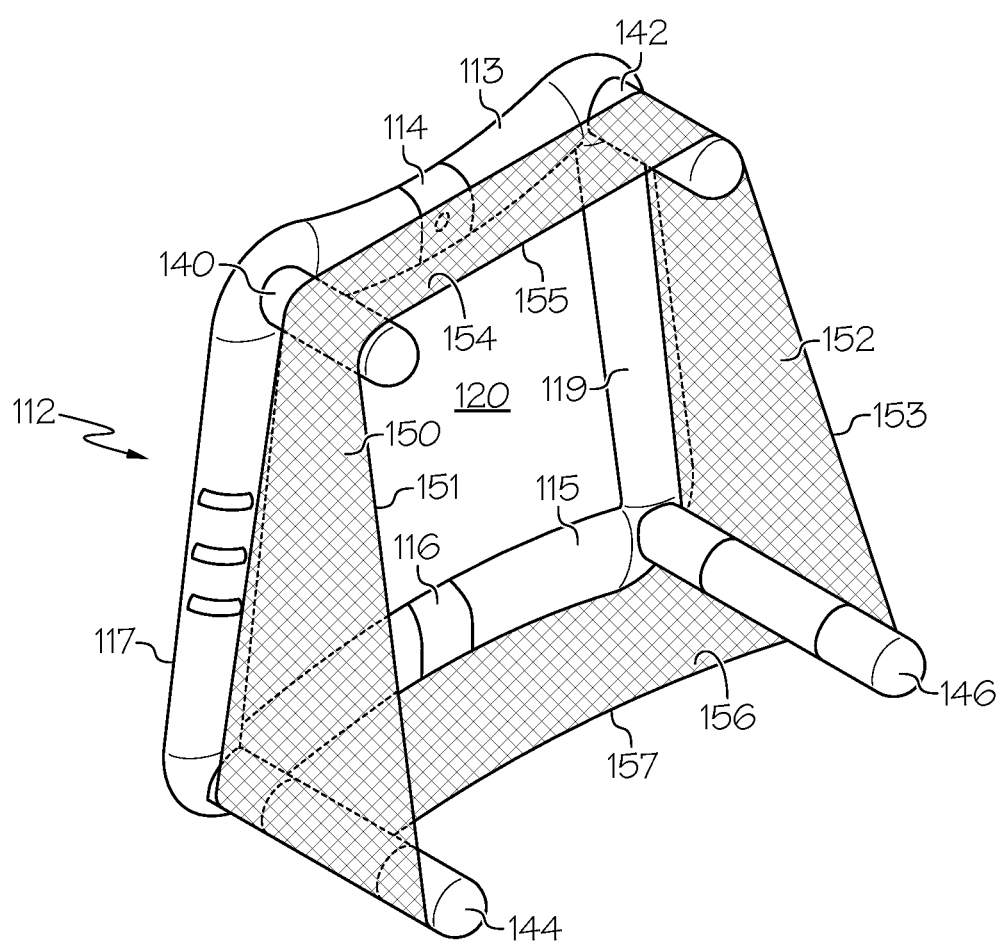
FIG. 8 is a frontal perspective view of an alternative embodiment of the inventive retractor having four side walls.

In alternative embodiments, illustrated in FIG. 7 and FIG. 8, the inventive retractor can be used without the absorbent pad or panel 20. For example, in addition to providing improved exposure and enhanced visualization of an episiotomy or vaginal laceration, improved vaginal retractors are needed for other gynecological procedures to help the surgeon visualize, inspect, repair and/or remove a portion of the lower internal genital organs. Common gynecological procedures and surgeries that could benefit from an improved vaginal retractor include, but are not limited to, loop electrosurgical excision procedure (LEEP procedures), uterine manipulator placement for laparoscopic/robotic hysterectomies, colposcopies, D&C procedures, cervical biopsies, and PAP tests.

Typically a vaginal speculum is used during such a gynecological procedure, being introduced into a patient's vagina to separate the vaginal walls and allow the lower internal genital organs to be examined. Metal, autoclavable duck-bill specula are conventionally used for such procedures. These units, with exposed joints, sharp edges, and cold metal are universally disliked by patients. The hinged joints and blade edges often pinch, scrape, or otherwise traumatize the delicate, supporting tissues in the area being examined. The conventional metallic specula blades are typically opaque, so that the only area available for inspection with a metallic speculum is the open end, for cervical examination, and the vaginal wall areas between the blades.

In an attempt to eliminate such problems, the vaginal retractor embodiments shown in FIGS. 7-8 can be used for gynecological procedures such as those listed above, and can be particularly useful for LEEP procedures and uterine manipulator placement for laparoscopic/robotic hysterectomies. A LEEP procedure is performed by a surgeon to remove abnormal tissue from the cervix. It may be done to confirm a cancer diagnosis or treat precancerous conditions of the cervix. During a LEEP, a thin wire loop is used to excise abnormal tissue. The cervix is then cauterized to stop any bleeding, and the remaining area usually heals in 4 to 6 weeks. Uterine manipulators are frequently preferred in laparoscopic hysterectomy because they reduce the incidence of ureteral injuries and facilitate colpotomy (an incision in the back wall of the vagina). In addition, uterine manipulators are used in diagnostic procedures that require the anteroposterior and lateral movements of the uterus, tubal ligation, and laparoscopic excision of ovarian masses and uterine fibroids. As a result, uterine manipulators are frequently used in many operative or diagnostic gynecological laparoscopic procedures because they are thought to reduce complications by facilitating dissection and increasing the field of view of the surgeon.

Like the retractor illustrated in FIGS. 1-6, the retractor embodiments shown in FIGS. 7 and 8 include a frame 112 for positioning within the vaginal canal. The frame 112 is defined by an upper support 113, a lower support 115, a right lateral support 117, and a left lateral support 119. The supports are preferably connected at their ends to form a four-sided frame 112 defining a central aperture 120 within its inner perimeter. The frame 112, as illustrated, is biased in the open position and the supports 113, 115, 117, 119 are oriented substantially in a single plane. However, unlike the previous embodiments described above, the central aperture 120 illustrated in FIG. 7 and FIG. 8 is not spanned or otherwise covered by a panel (20, see, e.g., FIG. 5). With physical access through the central aperture 120 of the frame, the user is provided with improved exposure and visualization of the internal female lower reproductive system, and a wire loop or uterine manipulator can easily be passed.

Each of the four corners of the frame 112 of FIGS. 7 and 8 have projections, specifically, a right upper anterior stability post 140, a left upper anterior stability post 142, a right lower anterior stability post 144, and a left lower anterior stability post 146. The anterior stability posts 140, 142, 144, 146 extend substantially perpendicularly from the plane of the open frame 112, and are preferably made of a rigid plastic material similar to or the same as the frame supports 113, 115, 117, 119. The frame supports and the anterior stability posts function to support and retract the vaginal tissues during use, so that the user can visualize the cervix, uterus, vaginal walls, etc. through the central aperture 120. To provide a wider base and more stability to the frame when inserted past the introitus and deeper into the vaginal canal, the lower anterior stability posts 144 and 146 can be longer and thus extend farther out from the plane of the frame 112 than the upper anterior stability posts 140, 142, as illustrated in FIG. 7 and FIG. 8. In addition, the distal ends of the lower anterior stability posts 144, 146 can be outwardly curved or otherwise biased in an outward direction to help prevent the lateral vaginal walls from obscuring the central aperture. The angle of the outward curve can be between about 10 degrees and about 90 degrees, and is illustrated at about a 45 degree angle. This curved design of the lower anterior stability posts 144, 146 can provide more stability to the frame when inserted, giving the retractor an improved ability to restrain the lateral and posterior vaginal walls from obscuring the view through the central aperture 120.

The embodiments of FIG. 7 and FIG. 8 also include a plurality of walls in the form of plastic barriers, sheets, nets, or webbings, specifically, a right side wall 150, a left side wall 152 and an upper wall 154. FIG. 8 also shows a lower wall 156. Each of the walls 150, 152, 154, 156 is generally quadrilateral in shape, connected at three of its sides to the frame, and extends substantially perpendicularly from the plane of the open frame. As illustrated, the right side wall 150 extends between the right upper anterior stability post 140 and the right lower anterior stability post 144. The right side wall 150 has one free side 151, i.e. a side not connected to the frame, with the three remaining sides respectively connected to the lengths of the right lateral support 117, the right upper anterior stability post 140, and the right lower anterior stability post 144. The left side wall 152 extends between the left upper anterior stability post 142 and the left lower anterior stability post 146, and having one free side 153 with the three remaining sides respectively connected to the left lateral support 119, the left upper anterior stability post 142, and the left lower anterior stability post 146.

The upper wall 154 as illustrated extends between the right upper anterior stability post 140 and the left upper anterior stability post 142, including one free side 155 with the three remaining sides respectively connected to the upper support 113, the right upper anterior stability post 140, and the left upper anterior stability post 142. The right side wall 150 and left side wall 152 provide additional means, by way of additional vaginal sidewall retraction, for the frame 112 to restrain or otherwise hold back vaginal or labial tissues from obscuring or obstructing the user's view through the central aperture 120. Similarly, the upper wall 154 can provide retraction of tissues such as the anterior vaginal wall. Like the extended lower stability posts, the walls can provide more stability to the frame when inserted past the introitus and deeper into the vaginal canal, and can prevent the vaginal walls from obscuring the central aperture The embodiment in FIG. 8 is similar to that of FIG. 7, but further includes the lower wall 156. As illustrated, the lower anterior stability posts 144, 146 can project straight outward, without the distal curves of the embodiment shown in FIG. 7. The lower wall 156 extends between the right lower anterior stability post 144 and the left lower anterior stability post 146 and allows the retractor to hold back tissues of the posterior vaginal wall from obscuring the user's view through the central aperture 120. Similar to the embodiment of FIG. 7, the embodiment of FIG. 8 also includes a right side wall 150, a left side wall 152 and an upper wall 154, as described above. When the frame 112 is in the closed or collapsed position, the right and left side walls 150, 152 can remain substantially straight or rigid when the retractor is folded, but the upper wall 154 and lower wall 156 should be made of a material that is forgiving enough so that it can fold or otherwise bias inward towards the center of the frame when the frame is folded (upper wall 154 folds down, and lower wall 156 folds up), so that they do not obstruct the retractor during insertion.

The embodiments illustrated in FIGS. 7 and 8, while specifically designed for deeper placement into the vaginal canal, can be used for any gynecological procedures involving the lower internal genital organs. More specifically, the inventive device as illustrated in FIGS. 7-8 can be manufactured to include an absorbent pad 20 (as described for FIGS. 1-6, above) spanning the central aperture. This can be useful for absorbing blood and other fluids during a vaginal repair. As a non-limiting example, if an episiotomy laceration in the posterior vaginal wall needs to be repaired, an absorptive gauze panel 20 as described earlier herein can be attached to the frame illustrated in FIG. 7 to cover the central aperture 120. Since this retractor includes side walls 150, 152 and upper wall 154 but no lower wall, it provides excellent exposure of the lacerated posterior vaginal wall. In contrast, the retractor illustrated in FIG. 8, having four walls 150, 152, 154 and 156 and an open central aperture 120 can be more useful for allowing the surgeon to view and surgically access the interior of the vagina during a LEEP procedure. In such a procedure, inclusion of a frame with the fourth, lower wall 156 as illustrated in FIG. 8 can be useful for restraining the posterior vaginal wall from obscuring the user's view through the central aperture 120.

The frame supports 113, 115, 117, 119 of the embodiments illustrated in FIGS. 7 and 8 preferably have a thickness and/or width which prevents failure of the frame when in the open position, i.e. failure of the supports that may be caused by the application of lateral pressure or stress exerted by the vaginal walls during a gynecological procedure. As noted above, the frame 112 is biased or predisposed to assume an expanded or open position, but can be folded or otherwise manually compressed or collapsed by a user into a closed position (see, e.g., FIGS. 3A and 3B). Both the upper support 113 and the lower support 115 include bendable central crimps 114 and 116 made of a plastic or elastomer which is less rigid in nature than the frame supports. Nevertheless, the stiffness of the crimps can be such that bending of the crimps 114, 116 only occurs when a certain manual force is applied to overcome the resistance provided by the crimps. For example, preferably the crimps are made of a semi-rigid but flexible plastic material that will not bend under the lateral pressure forces of the vaginal walls, yet can be caused to bend when a directed force is applied by the user.

The crimps 114, 116 can be of soft to medium hardness (e.g. 35-60 Shore A) so that they can be bendable but, as noted above, biased to straighten out and to return the frame to a substantially open configuration, while the supports 113, 115, 117, 119 and stability posts 140, 142, 144, 146 can be comparatively more rigid, measuring on the high end of the hardness scale (e.g. 75-100 Shore A). Each of the webs or walls 150, 152, 154, 156 illustrated in FIGS. 7 and 8 can be made of a material similar to that of the crimps 114, 116, so that they are flexible yet strong enough to resist vaginal wall pressures.

The present invention provides an improved apparatus and method for performing a vaginal repair which improves access and visualization of the repair site, is configured to minimize slippage during use, and which is lightweight and minimizes discomfort to the patient. It also provides a means to absorb or prevent blood/fluids entering the surgical field, is inexpensive to manufacture and maintain, and can be utilized by health care professionals having various skill levels. While the present invention has been illustrated by the description of particular embodiments in considerable detail, it is not intended to restrict or limit the scope of the appended claims to such detail. Additional advantages and modifications will be readily apparent to those skilled in the art without departing from the concept or scope of the invention.

What is claimed is:

1. A retractor for gynecological procedures involving the lower internal genital organs, the retractor comprising:
 a) a frame defining a central aperture, the frame including an upper support, a lower support, a right lateral support, a left lateral support, a right upper anterior stability post, a left upper anterior stability post, a right lower anterior stability post, and a left lower anterior stability post, wherein the lower anterior stability posts are longer than and extend farther out from the plane of the frame than the upper anterior stability posts, wherein the frame is biased to assume an open position in which the supports are oriented substantially in a single plane, and wherein each of the anterior stability posts extend substantially perpendicularly from the plane of the open frame; and
 b) a plurality of walls for restraining vaginal tissues from obstructing the central aperture, wherein each of the plurality of walls is connected to the frame and extends substantially perpendicularly from the plane of the open frame, and wherein the frame can be folded into a closed position for insertion into the vaginal canal.

2. The retractor of claim 1, wherein the lower anterior stability posts are outwardly curved.

3. The retractor of claim 1, wherein the plurality of walls comprises:
 a) a right side wall located between the right upper anterior stability post and the right lower anterior stability post;
 b) a left side wall located between the left upper anterior stability post and the left lower anterior stability post; and
 c) an upper wall located between the right upper anterior stability post and the left upper anterior stability post.

4. The retractor of claim 3, wherein the right side wall is connected to the frame at the right lateral support, the right upper anterior stability post, and the right lower anterior stability post, wherein the left side wall is connected to the frame at the left lateral support, the left upper anterior stability post, and the left lower anterior stability post, and wherein the upper wall is connected to the frame at the upper support, the right upper anterior stability post, and the left upper anterior stability post.

5. The retractor of claim 3, wherein the plurality of walls further comprises:
 d) a lower wall located between the right lower anterior stability post and the left lower anterior stability post, wherein the lower wall is connected to the frame at the lower support, the right lower anterior stability post, and the left lower anterior stability post.

6. The retractor of claim 5, wherein the compliant panel is an absorbent pad made of a semi-permeable material useful for absorbing blood and other fluids.

7. The retractor of claim 1, further comprising a compliant panel spanning the central aperture.

8. The retractor of claim 1, wherein the lower support, the right lateral support, and the left lateral support are substantially the same length, and wherein the upper support is shorter in length than the lower support, so that the overall shape of the frame is trapezoidal when in the open position.

9. The retractor of claim 1, wherein the upper support includes a central upper crimp and the lower support includes a central lower crimp, the crimps being biased to bend when a force is applied by the user and to straighten when the force is released.

10. The retractor of claim 1, wherein the right lateral support and the left lateral support include raised semi-circular ridges protruding from the outer circumference of the lateral supports to reduce slippage of the frame within the vaginal canal.

11. A retractor for gynecological procedures involving the lower internal genital organs, the retractor comprising:
a) a frame defining a central aperture, the frame including:
i) an upper support including a central upper crimp;
ii) a lower support including a central lower crimp, wherein the central upper crimp and the central lower crimp are biased to bend when a force is applied by a user and to straighten when the force is released;
iii) a right lateral support;
iv) a left lateral support, wherein the upper support, the lower support, the right lateral support, and the left lateral support are connected to form the frame defining the central aperture;
v) a right upper anterior stability post;
vi) a left upper anterior stability post;
vii) a right lower anterior stability post; and
viii) a left lower anterior stability post; wherein the frame is biased to assume an open position in which the supports are oriented substantially in a single plane, and wherein each of the anterior stability posts extend substantially perpendicularly from the plane of the open frame; and
b) a plurality of walls for restraining vaginal tissues from obstructing the central aperture, wherein each of the plurality of walls is connected to the frame and extends substantially perpendicularly from the plane of the open frame, the plurality of walls comprising:
i) a right side wall located between the right upper anterior stability post and the right lower anterior stability post;
ii) a left side wall located between the left upper anterior stability post and the left lower anterior stability post; and
iii) an upper wall located between the right upper anterior stability post and the left upper anterior stability post, wherein the frame can be folded into a closed position for insertion into the vaginal canal.

12. The retractor of claim 11, wherein the lower anterior stability posts are longer than and extend farther out from the plane of the open frame than the upper anterior stability posts.

13. The retractor of claim 11, wherein the lower anterior stability posts are outwardly curved.

14. The retractor of claim 11, wherein the right side wall is connected to the frame at the right lateral support, the right upper anterior stability post, and the right lower anterior stability post, wherein the left side wall is connected to the frame at the left lateral support, the left upper anterior stability post, and the left lower anterior stability post, and wherein the upper wall is connected to the frame at the upper support, the right upper anterior stability post, and the left upper anterior stability post.

15. The retractor of claim 11, the plurality of walls further comprising:
iv) a lower wall located between the right lower anterior stability post and the left lower anterior stability post, wherein the lower wall is connected to the frame at the lower support, the right lower anterior stability post, and the left lower anterior stability post.

16. The retractor of claim 11, further comprising a compliant panel spanning the central aperture.

17. The retractor of claim 16, wherein the compliant panel is an absorbent pad made of a semi-permeable material useful for absorbing blood and other fluids.

18. The retractor of claim 11, wherein the lower support, the right lateral support, and the left lateral support are substantially the same length, and wherein the upper support is shorter in length than the lower support, so that the overall shape of the frame is trapezoidal when in the open position.

* * * * *